United States Patent [19]

Okada et al.

[11] 4,254,227
[45] Mar. 3, 1981

[54] PROCESSES FOR PRODUCING SYRUPS OF SYRUP SOLIDS CONTAINING FRUCTOSE-TERMINATED OLIGOSACCHARIDES

[75] Inventors: Shigetaka Okada, Ikoma; Sumio Kitahata, Ibaragi; Shigeharu Yoshikawa, Osaka; Kentaro Miyake, Okayama, all of Japan

[73] Assignee: Kabushiki Kaisha Hayashibara Seibutsu Kagaku Kenkyujo, Okayama, Japan

[21] Appl. No.: 18,675

[22] Filed: Mar. 8, 1979

[30] Foreign Application Priority Data

Mar. 9, 1978 [JP] Japan ................... 53-26017

[51] Int. Cl.³ .............................................. C12P 19/18
[52] U.S. Cl. ..................... 435/97; 435/193; 435/832; 435/835; 435/837; 435/852; 435/838
[58] Field of Search ................... 435/97, 193, 177–182

[56] References Cited

U.S. PATENT DOCUMENTS

| 3,701,714 | 10/1972 | Okada et al. | 435/193 X |
|---|---|---|---|
| 3,703,440 | 11/1972 | Okada et al. | 435/193 X |
| 3,728,132 | 4/1973 | Tsuyama et al. | 435/99 X |
| 3,894,146 | 7/1975 | Tsuyama | 424/49 |
| 3,923,598 | 12/1975 | Horikoshi | 195/31 |
| 3,988,206 | 10/1976 | Shiosaka | 195/62 |
| 4,135,977 | 1/1979 | Horikoshi et al. | 195/7 |

FOREIGN PATENT DOCUMENTS 1390065  4/1975  United Kingdom .

OTHER PUBLICATIONS

Arch. Microbiol. vol. 111, p. 271–282 (1977).
Nakamura et al., Biotechnology and Bioengineering vol. 19, pp. 87–99 (1977).
Barman, Enzyme Handbook vol. I, p. 320 (1969).
Nakamura et al. Chemical Abstracts vol. 86, 876575 (1977).

*Primary Examiner*—Lionel M. Shapiro
*Attorney, Agent, or Firm*—Browdy and Neimark

[57] ABSTRACT

The present invention relates to processes for producing syrups or syrup solids containing fructose-terminated oligosaccharides, characterized by subjecting a mixture containing liquefied starch and either fructose or sucrose to the action of immobilized cyclodextrin glucanotransferase E.C. 2.4.1.19.

3 Claims, 2 Drawing Figures

PROCESSES FOR PRODUCING SYRUPS OF SYRUP SOLIDS CONTAINING FRUCTOSE-TERMINATED OLIGOSACCHARIDES

DETAILED DESCRIPTION OF THE INVENTION

Figure 1:
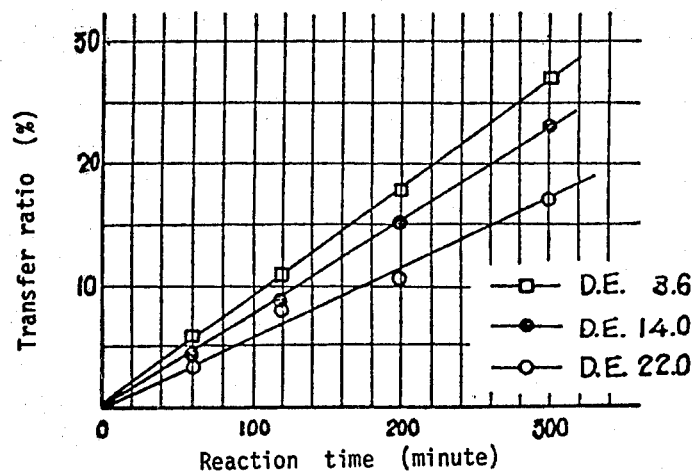

The present invention relates to processes for producing syrups or syrup solids containing fructose-terminated oligosaccharides (hereinafter abbreviated SFTO), characterized by subjecting a mixture containing liquefied starch and either fructose or sucrose to the action of immobilized cyclodextrin glucanotransferase E.C. 2.4.1.19 (hereinafter abbreviated as CGT).

As described in Japanese Unexamined Patent Publication Nos. 72-20373, 75-63189 and 75-88290, and by Hans Bender, Arch. Microbiol. vol. 111, pp. 271–282 (1977), CGT is produced by bacteria of genus Bacillus such as *Bacillus macerans, Bacillus megaterium, Bacillus circulans, Bacillus polymyxa* and *Bacillus stearothermophilus*, and genus Klebsiella such as *Klebsiella pneumoniae*.

It is also known that SFTO are produced by subjecting a mixture containing liquefied starch and either fructose or sucrose to the action of a CGT solution whereby the glucosidic residues of the dextrin molecules in the liquefied starch are transferred to the fructose or sucrose molecules (e.g., see Japanese Unexamined Patent Publication No. 72-20373).

It is also known from Japanese Unexamined Patent Publication No. 75-12272, Japanese Examined Patent Publication Nos. 74-40949 and 74-40950 that SFTO obtained with CGT have various and diverse uses as a sweetener, and that although SFTO are digestible and absorbable in vivo they are new sweeteners that is, unlike sucrose, low cariogenic or low dental-caries inducing.

The present inventors screened and studied processes feasible for producing the useful SFTO. The studies resulted in the clarification that at least three reactions occur when a mixture containing liquefied starch and either fructose or sucrose is subjected to the action of an aqueous CGT solution to produce SFTO.

The reactions are:

"Reaction I": the reaction that produces cyclodextrins from the liquefied starch, "Reaction II": the reaction that transfers the glucosidic residues in the cyclodextrins formed by "Reaction I" to the fructose or sucrose molecules, and "Reaction III": the reaction that transfers directly the glucosidic residues in the liquefied starch to the fructose or sucrose molecules.

The inventors envisaged that SFTO can be produced more effectively and advantageously by relying mostly on "Reaction III", the reaction that transfers directly the glucosidic residues in the liquefied starch to the fructose or sucrose molecules than via cyclodextrin utilizing "Reactions I and II", and studied and investigated painstakingly processes for SFTO.

The inventors immobilized CGT by known methods in the art and found that the dextrinogenic activity per unit weight CGT protein decreases greatly in comparison to that of the intact enzyme (unimmobilized enzyme), whereas the alpha-cyclodextrin-decomposing activity hardly decreases or, in most cases, increases, and also that contact of immobilized enzyme increases drastically the transfer activity of glucosidic residues to fructose or sucrose to form SFTO very readily.

Particularly, it was found that the dextrinogenic activity per unit weight CGT protein decreases to about 10 to 30% when the enzyme is immobilized by the methods including the carrier-binding methods, the cross-linking methods and the entrapping methods, whereas the alpha-cyclodextrin-decomposing activity hardly decreases or increases to about 80 to 130% as compared with that of the intact enzyme.

Also was found that when a given substrate solution containing liquefied starch and either fructose or sucrose in the same proportions and concentrations is allowed to react under the same conditions with either immobilized or intact enzyme in the same amount of alpha-cyclodextrin-decomposing activity per unit weight liquefied starch, the employment of immobilized enzyme results in a remarkably faster rate of transfer action per unit weight CGT protein than intact enzyme.

In other words, it was found that a much higher rate of SFTO formation per unit weight enzyme protein is realizable with the employment of immobilized enzyme.

The invention has one important feature that the amount of enzyme protein required to attain the same formation ratio (throughout the Specification, the formation ratio is expressed as transfer ratio) of SFTO can be reduced to about 1/1.5~1/5 when immobilized enzyme is used instead intact enzyme.

The present invention will be illustrated in further details.

CGT used in the invention is obtained by cultivating microorganisms capable of producing CGT, for example, bacteria of genus Bacillus and genus Klebsiella, in a nutrient medium containing carbon source(s), nitrogen source(s), mineral(s) and vitamin(s), and recovering the formed CGT by known methods, for example, either by centrifuging or filtering the culture broth and collecting supernatant or filtrate containing the enzyme or by recovering the biomass from the culture broth, extracting the enzyme from the biomass and collecting supernatant or filtrate containing the enzyme. If necessary, the crude enzyme solution may be purified by such known methods as salting-out, dialysis, adsorption on and desorption from starch, gel-filtration and/or ion-exchange chromatography.

The thus obtained crude or purified enzyme can be freely immobilized by such known methods as the carrier-binding methods, the cross-linking methods or the entrapping methods.

Employable carriers (matrices or supports) include natural organic macromolecules such as cellulose, starch, agar, sodium alginate, gelatin and derivatives thereof, synthetic organic macromolecules such as polyacryl amide, polyethylene glycol, polyaminopolystyrene and polyvinyl alcohol, and inorganic substances such as clay, alumina, glass ceramics and stainless steel.

Immobilization may be carried out by any method known in the art under pH and thermal stable conditions for CGT, for example, in a pH range of about 4 to 10 and temperature range below 70° C.

SFTO can be easily produced batchwise or continuously by subjecting a mixture containing liquefied starch and either fructose or sucrose to the action of an immobilized CGT.

In the invention, any starch is employable as material starch, regardless of its origin, e.g., cereal starch such as those from corn and wheat, and tuber or root starch such as those from sweet- and white potatoes. The starch is treated with acid or alpha-amylase to give a liquefied starch with a dextrose equivalent (D.E.) of about 3 to 40 which is used as a donor of glucosidic residues. The weight proportion of the acceptor containing ketose such as fructose or sucrose to liquefied starch ranges, preferably, from about 0.2 to 5, d.s.b. Single compound such as fructose or sucrose and mixtures such as those of isomerized sugar or invert sugar is employable as acceptor.

The preferable concentration range of the aqueous substrate solution containing the acceptor and the donor is about 10 to 50 w/w%. The presence of calcium salt of about $10^{-4}$ M to $10^{-2}$ M in the aqueous substrate solution stabilizes favorably the activities of CGT.

The preferable reaction conditions under which CGT reacts stably and sufficiently lie in the pH range of about 5 to 10 and the temperature range of about 30° to 70° C.

Usually, about one to 10,000 units of alpha-cyclodextrin-decomposing activity as defined later in the Specification per a liquefied starch, d.s.b., is used. The reaction is carried out usually for about 0.1 to 100 hours.

The aqueous SFTO solution obtained by the reaction is purified and either concentrated or dehydrated by known methods in the art to yield syrups or syrup solids. The products can be freely used as a sweetening agent, gustatory agent or taste improver for various foods, drinks, nutritives, confectioneries, oral medicines, cosmetics, dentifrices and gargles.

SFTO has the features of being noncrystallizable, desirably viscous and digestible and absorbable in vivo, but, unlike sucrose, low cariogenic.

The activities of CGT are defined as follows.

(a) Dextrinogenic Activity

A mixture prepared by adding 0.5 ml enzyme solution to 4.5 ml of a 0.55 w/w% soluble starch solution buffered at pH 5.5 is incubated at 40° C. for 10 min. A 0.5 ml aliquot of the reaction solution is withdrawn and admixed with 4 ml of a 0.01 M $I_2$-KI solution.

Then, water is added to the resultant to bring the total amount to 20 ml. The amount of enzyme which effects a 1% increase in the transmittance of the solution at 660 nm is defined as one unit of dextrinogenic activity.

(b) Alpha-cyclodextrin-decomposing Activity

A mixture prepared by adding 2 ml of 2.5 w/w% sucrose solution and 0.5 ml of enzyme solution to 2 ml of 1 w/w% alpha-cyclodextrin solution is incubated at 40° C. for a given time.

A 0.5 ml aliquot of the reaction solution is withdrawn and admixed with 0.1 ml of a solution (5 units) of commercially available crystalline glucoamylase. Then, the resultant is incubated at 40° C. for one hour to hydrolyze only the oligosaccharides having alpha-1,4-glucosidic linkages into glucose but not the alpha-cyclodextrin.

The amount of glucose is assayed by the Somogyi-Nelson method.

The amount of CGT which hydrolyzes one $\mu$ mole of alpha-cyclodextrin over a period of one minute is defined as one unit of alpha-cyclodextrin-decomposing activity.

The invention will be illustrated further with reference to the following Experiments.

Experiment 1. Preparation of CGT

A strain of *Bacillus megaterium* T 5 FERM-P No. 935 was inoculated on a liquid medium prepared according to the usual way and containing 1 w/v% wheat bran, 1 w/v% corn steep liquor, 0.5 w/v% dry yeast, 1 w/v% polypeptone, 0.25 w/v% ammonium sulfate, 4 w/v% soluble starch, 0.1 w/v% urea and 1.0 w/v% calcium carbonate, and the mixture was incubated at 37° C. for 60 hours with aeration and stirring.

CGT in the supernatant obtained from the culture broth showed a dextrinogenic activity of about 40 units per ml. The supernatant was cooled to about 3° C., admixed with about one half amount of cold acetone with stirring and formed a small amount of white precipitate.

The precipitate was removed from the mixture by centrifugation to give a supernatant. Twenty liters of the obtained supernatant was kept at 3° C., admixed with ammonium sulfate to give 30% saturation and formed again a small amount of white precipitate. The white precipitate was removed by centrifugation to give a supernatant. The supernatant was admixed with 300 g of corn starch and stirred for 20 min. to yield a suspension containing CGT adsorbed on starch.

The suspension was filtered through a filter layer prepared previously by mixing 700 g of corn starch with 500 g of diatomaceous earth, and the filter cake was washed away with a 30% saturated aqueous ammonium sulfate solution. The obtained starch was washed again with a cold 30 v/v% aqueous acetone solution, and the enzyme adsorbed on the starch was eluted with an M/30 aqueous disodium hydrogen phosphate solution. The eluate was admixed with ammonium and white precipitate was formed between 25 and 45% saturation. The white precipitate was collected and dehydrated to give a purified CGT preparation.

The specific activity of the CGT preparation calculated on dextrinogenic activity was about 60 times of that of the culture-broth supernatant. The yield of the activity was about 65%.

Experiment 2. Immobilization of CGT

Ten grams of a commercially available cyanogen bromideactivated Sepharose 4B (Pharmacia Fine Chemicals, Uppsala, Sweden) was washed with 2,000 ml of a $10^{-3}$ M aqueous hydrochloric acid solution. A mixture prepared by adding the washed cyanogen bromide-activated Sepharose 4B to about 50 ml of a 0.1 M borate buffer solution, pH 8.3, containing 0.5 M sodium chloride and 100 mg of purified CGT preparation as protein obtained by the method described in Experiment 1, was allowed to react to immobilize CGT at room temperature with stirring. The immobilized CGT collected by filtration was resuspended in 200 ml of a 1 M aqueous ethanolamine solution, pH 9.0, and occasionally stirred for 2 hours.

Subsequently, the immobilized enzyme was collected by filtration and washed sufficiently, alternately and repeatedly with an acetate buffer, pH 4.0, containing 0.5 M sodium chloride and a 0.1 M borate buffer, pH 8.3, containing 0.5 M sodium chloride.

The thus obtained enzyme was determined as about 50.8 mg protein by measuring the amount of CGT protein that flowed away in the filtrates and washings.

Therefore, the immobilization ratio of CGT was about 50.8%.

The inventors found that the intact enzymatic activities per unit weight enzyme protein vary remarkably and disproportionately upon immobilization. For details refer to the results given in Table 1.

TABLE 1

|   | | Dextrinogenic activity | Alpha-cyclodextrin-decomposing activity |
|---|---|---|---|
| a. | Total activity of CGT used for immobilization, units | 14,000 | 67,800 |
| b. | Amount of CGT immobilized, units | 7,100 | 34,400 |
| c. | Retained activity of immobilized CGT, units | 1,000 | 40,200 |
| d. | Ratio of retained activity, % | 14 | 117 |

Notes:
b. Amount of CGT immobilized, units = (a. Total activity used for immobilization, units) × 0.508
d. Ratio of retained activity, % = (c. Retained activity of immobilized CGT, units) ÷ (b. Amount of immobilized CGT, units) × 100

This led to the discovery of the phenomenon that immobilization decreases extremely the dextrinogenic activity of CGT, but increases its alpha-cyclodextrin-decomposing activity per unit weight enzyme protein.

Although the mechanism of the phenomenon is still unclarified, it is presumed that among the three aforementioned "Reactions I, II and III", "Reaction II" is especially accelerated by the immobilization.

While the pH thermal stability limits for intact enzyme are respectively about 6~8 and up to about 50° C., immobilization stabilizes the enzyme and extends the limits to about pH 5~9 and about 55° C.

Experiment 3. Transfer action of immobilized CGT

Substrate solutions containing 5 w/w% sucrose (acceptor) and 5 w/w% liquefied starch (donor) with respective D.E. 3.6, 14.0 or 22.0 were prepared. Five ml aliquots of each substrate solution were admixed with 130 units of alpha-cyclodextrin-decomposing activity (retained activity) of either purified intact CGT (about 0.19 mg) obtained by the method described in Experiment 1 or immobilized CGT (about 0.16 mg) obtained by the method described in Experiment 2, and the mixtures were incubated at pH 6.0 and 40° C. with shaking.

The incubation mixtures were sampled occasionally during the incubation to determine the transfer ratio of glucosidic residues to sucrose by paper chromatography.

The transfer ratio was determined using the following equation:

$$T = (A/B) \times 100,$$

where T is transfer ratio, A the amount of acceptor to which glucosidic residues are transfered and B the total amount of acceptor used as substrate.

Figure 2:
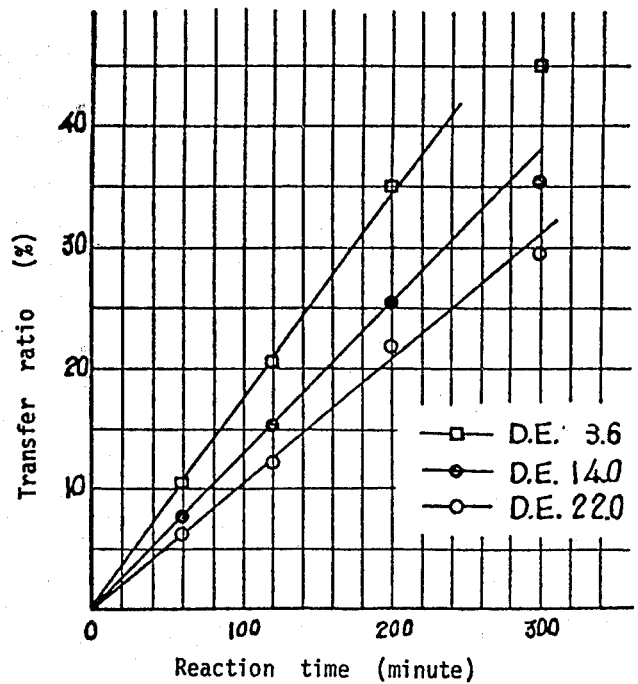

The results are shown in FIGS. 1 and 2.

FIG. 1 shows the results of the experiments using purified intact CGT as control and FIG. 2 the results of the experiments of the invention using immobilized enzyme.

As is clear from the results shown in FIGS. 1 and 2, using the same amounts of alpha-cyclodextrin-decomposing activity, immobilized CGT attained, under reaction conditions wherein less unit weights of enzyme protein was used, an approximately two times higher transfer ratio in comparison to that attained with intact enzyme.

As described in Experiment 2, although the mechanism of the phenomenon is still unclarified, it is presumed from the present experiment that the immobilization of CGT accelerates remarkably and especially the aforementioned "Reaction III" of CGT, i.e., the reaction that transfers directly the glucosidic residues in the liquefied starch (donor of glucosidic residues) to the fructose or sucrose (acceptor of glucosidic residues).

The amount of CGT required to attain a 20% transfer ratio was determined according to the method described in Experiment 3 under conditions wherein the transfer ratio varies in proportion to the amount of CGT used. The inventors found that a given transfer ratio is attainable with immobilized CGT using a half of the amount of CGT protein required for intact CGT.

This means that immobilization of CGT extremely increases the transfer activity per protein. Therefore, the reaction time can be shortened drastically with immobilized enzyme.

In addition, the inventors found that CGT can be immobilized in very high enzyme protein concentration, about 0.1 to 10 w/w%, hardly loosing its activities, and that the objective of the invention is readily achievable by subjecting the substrate solution to the enzymatic reaction briefly, due to the high activity per g immobilized enzyme.

The immobilized CGT can be used readily in a continuous system. For example, column-reaction containers packed with the enzyme and operated continuously are extremely advantageous for mass producing SFTO at a low cost.

As is clear from FIGS. 1 and 2, the lower the D.E. of the liquefied starch the higher will the transfer ratio be.

Liquefied starch with D.E. less than about 2, however, is liable to degradation and renders difficulty in the enzymatic reaction. When liquefied starch with a D.E. of 40 or higher is used, the resulting transfer ratio and SFTO production decrease.

A few examples are shown below.

EXAMPLE 1

Thirty units per g liquefied starch based on alpha-cyclodextrin-decomposing activity of immobilized enzyme obtained by the method in Experiment 2 was added to an aqueous solution containing 20 w/w% liquefied starch, D.E. 5, and 10 w/w% sucrose. The resultant mixture was incubated in a batchwise operation at pH 6.0 and 50° C. for 48 hours with gentle stirring.

One portion of filtrate obtained by filtering out the immobilized enzyme from the reaction solution could be purified with extreme ease by any usual purification method in the art for saccharides, i.e., decolorizing with activated carbon and then desalting with ion-exchangers (—H and —OH types).

Subsequently, the resultant was concentrated under reduced pressure to give SFTO in syrup form (Product A) with a water content of 20 w/w%.

The transfer ratio of SFTO product was about 60% and the yield was 90%, d.s.b. against the substrate consisting of liquefied starch and sucrose.

The syrup had a mild sweetness and high viscosity.

Another portion of the above filtrate was subjected to the actions of small amounts of commercially available alpha- and beta-amylases, and the resultant was purified and concentrated similarly to give SFTO in syrup form (Product B) with substantially the same transfer ratio. The product A was more easier to handle because its viscosity was about two third that of the Product B described above.

EXAMPLE 2

A strain of *Bacillus macerans* IFO 3490 was inoculated on a liquid medium containing 1 w/v% corn steep liquor, 1 w/v% soluble starch, 0.5 w/v% ammonium sulfate and 0.5 w/v% calcium carbonate, and the resultant mixture was incubated at 37° C. for 3 days with aeration and stirring. The supernatant containing CGT obtained by centrifuging the culture broth was purified according to the methods described in Experiment 1.

The specific activity of the purified enzyme preparation based on dextrinogenic activity was about 30 times higher than that of the culture-broth supernatant. The yield of dextrinogenic activity was about 70%.

In addition, an about 10 w/w% aqueous gelatin solution was prepared by heating to about 60° C. and cooling to about 40° C. The gelatin solution was admixed with the enzyme preparation described above to give a mixture solution with an enzyme protein concentration of about 0.5 w/w%, which was poured into toluene, precooled to 4° C., to solidify the gelatin into bead form. The bead-form solid was recovered from the resultant by filtration, and was washed successively with n-propyl alcohol and cold water. Ten grams of the bead-form solid was dipped in 150 ml of a 2.5 w/w% aqueous glutaraldehyde solution and allowed standing at a room temperature for 30 min. to react with glutaraldehyde. The product was collected by filtration and excess glutaraldehyde was removed with a large amount of water to give immobilized enzyme.

A slight amount of protein was detected in the filtrates and washings. The immobilization ratio was nearly 100%. The retained activity ratios of the immobilized enzyme were about 21% based on dextrinogenic activity and about 102% based on alpha-cyclodextrin-decomposing activity. The amount of enzyme protein required to attain the 20% transfer ratio described in Experiment 3 decreased to about 1/1.5 by the immobilization. The immobilized enzyme was packed in a column with a diameter to height ratio of 1:3. A mixture containing 15 w/w% liquefied starch, D.E. 10, and 10 w/w% fructose was allowed to react with the immobilized enzyme by continuous passage through the column at 50° C., pH 6.0 and a flow rate of SV 2. The transfer ratio hardly varied throughout the reaction which was operated for one week and at the end of the reaction it was about 55%.

The resultant reaction mixture was purified and concentrated similarly as in Example 1, lyophilized and pulverized, whereby a white powder SFTO product was obtained in a yield of about 93%, d.s.b. against the substrate.

Alternatively, in addition to bead form, the gelatin solution containing the enzyme as prepared in this Example can be easily shaped into any form or shape such as fiber, film and tube according to known methods. Regardless of its shape or form, the thus immobilized enzyme can be used in the production of SFTO without imparting any difference to the product.

EXAMPLE 3

A strain of *Bacillus stearothermophilus* TC-60 FERM-P No. 2222 was inoculated on a liquid medium containing 2 w/v% soluble starch, 0.5 w/v% ammonium chloride, 0.05 w/v% dipotassium phosphate, 0.025 w/v% magnesium sulfate. $7H_2O$, and 0.5 w/v% calcium carbonate, and the resultant mixture was incubated at 50° C. for three days with aeration and stirring. The supernatant containing CGT obtained by centrifuging the culture broth was purified according to the method described in Experiment 1.

The specific activity of the purified CGT based on dextrinogenic activity was about 50 times higher than that of the supernatant. The yield of dextrinogenic activity was about 90%.

Powder aluminium oxide ($\gamma$-$Al_2O_3$), about 0.1 to 0.5 mm in particle size, was kept in a 5 w/w% aqueous nitric acid solution at 90° C. for 2 hours, washed sufficiently with distilled water, then successively with methanol and ether, and air-dried to give activated aluminium oxide. The obtained activated aluminium oxide was allowed to react with 10 v/v% 3-aminopropyltriethoxysilane in toluene for 5 hours under refluxing and heating conditions. The formed alkylamine alumina was recovered by filtration, washed successively with toluene and ether, and air-dried.

One thousand grams of alkylamine alumina (carrier) was dipped in a 1.25 w/w% aqueous glutaraldehyde solution buffered with a 0.1 M phosphate buffer, pH 7.0, and kept at room temperature for one hour. The resultant carrier was collected by filtration, washed thoroughly with water, added to a 0.1 M acetate buffer, pH 6.0, containing 100 g of the CGT described above, and then allowed standing at 8° C. for 16 hours to immobilize the enzyme. The immobilized enzyme was recovered by filtration, washed with water and used in the following transfer reaction. The immobilization ratio determined by calculating the amounts of protein that flowed away in the filtrates and washings was about 75%. The retained activity ratios of the immobilized enzyme were about 17% based on dextrinogenic activity and about 125% based on alpha-cyclodextrin-decomposing activity. The amounts of enzyme protein required to attain the 20% transfer ratio according to the method described in Experiment 3 decreased to about one third by the immobilization.

The immobilized enzyme was packed in a column with a diameter to height ratio of 1:10. A mixture containing 20 w/w% liquefied starch, D.E. 8, 20 w/w% fructose and $10^{-3}$ M calcium chloride was allowed to react with the immobilized enzyme by continuous passage through the column at pH 6.0, 65° C. and a flow rate of SV 4. The transfer ratio was hardly varied throughout the reaction which was operated for 7 weeks and at the end of the reaction it was about 60%.

The resultant reaction mixture was purified and concentrated similarly as in Example 1 and spray dried, whereby a mild sweet SFTO product in white powder form, homogenous in particle size, was obtained in a yield of about 91%, d.s.b. against the substrate.

EXAMPLE 4

Alkylamine porous glass powder was prepared similarly as in Example 3 except using porous glass powder (Bio-Glas 500, Bio-Rad Laboratories, U.S.A.) instead of aluminium oxide. Fifty grams of the alkylamine porous glass powder was dipped in an aqueous glutaraldehyde solution containing 3 g of purified CGT preparation obtained by the method described in Experiment 1 to yield immobilized enzyme.

The immobilization ratio determined by calculation similarly as in Example 3 was about 80%. The retained activity ratios were about 11% based on dextrinogenic activity and about 108% based on alpha-cyclodextrindecomposing activity. The amount of enzyme protein required to attain 20% transfer ratio according to the method described in Experiment 3 decreased to about one half by the immobilization. The immobilized enzyme was packed in a column with a diameter to height ratio of 1:8. A mixture containing 20 w/w% liquefied starch, D.E. 20, and 20 w/w% glucose isomerized sugar (containing about 12 w/w% glucose and about 8 w/w% fructose) was allowed to react with the immobilized enzyme by continuous passage through the column at pH 6.5, 50° C. and a flow rate of SV 2. The transfer ratio was approximately constant throughout the reaction which was operated for 5 weeks and at the end of the reaction it was about 45% to fructose.

The resultant reaction mixture was purified and concentrated similarly as in Example 1, vacuum dried and pulverized, whereby a mild sweet SFTO product in white powder form was obtained in a yield of about 95%, d.s.b. against the substrate.

EXAMPLE 5

Fifty grams of alkylamine porous glass powder (carrier) prepared in Example 4 was allowed to react with a mixture consisting of 50 g of p-nitrobenzoylchloride, 80 ml of triethylamine, and 1170 ml of chloroform for 5 hours under refluxing and heating conditions.

Then, the resultant carrier was washed successively with chloroform and ether, air-dried, and placed in a boiling 5 w/w% sodium hydrosulfite solution for 4 hours and then washed with water.

The obtained arylamine porous glass was added to 1,000 ml of a 2 N aqueous hydrochloric acid solution. The resultant mixture was kept at 0° C. in an ice bath and admixed to react with 5 g of sodium nitrite (solid).

After the reaction, the carrier was recovered by filtration, and excess acid and sodium nitrite were removed with ice water to obtain diazotized arylamine porous glass powder.

In addition, a 4,000 ml of mixture solution was prepared by mixing a 0.1 M carbonate buffer, pH 8.5, and 1 w/w% of the purified CGT preparation obtained by the method described in Example 3 and admixed with 40 g of the above obtained powder. The resultant was allowed standing at 0° C. for 5 hours with gentle stirring to immobilize the enzyme. The immobilized enzyme was recovered by filtration, washed sufficiently with water and used in the following transfer reaction. The immobilization ratio determined by calculation similarly as in Example 3 was about 68%. The retained activity ratios were 9% based on dextrinogenic activity and 98% based on alpha-cyclodextrindecomposing activity.

The amount of enzyme protein required to attain 20% transfer ratio according to the method described in Experiment 3 decreased to about one third by the immobilization. The immobilized enzyme was packed in a column with a diameter to height ratio of 1:10. A mixture containing 10 w/w% liquefied starch, D.E. 5, 30 w/w% sucrose, and $10^{-3}$ M calcium chloride was allowed to react with the immobilized enzyme by continuous passage through the column at pH 6.0, 65° C. and a flow rate of SV 3. The transfer ratio hardly varied throughout the reaction which was operated for 5 weeks and at the end of the reaction it was about 25%. The resultant reaction mixture was purified and concentrated similarly as in Example 1, whereby a strongly sweet SFTO in noncrystalline syrup form with a water content of about 17 w/w% was obtained in a yield of about 94%, d.s.b. against the substrate.

What we claim is:

1. A process for producing syrup or syrup solids containing fructose-terminated oligocaccharides, comprising subjecting a mixture solution of a liquefied starch, which acts as a donor of glucosidic residues, and one or more members selected from the group consisting of fructose, sucrose, isomerized sugar and invert sugar, which act as an acceptor for glucosidic residues, to the action of an immobilized cyclodextrin glucanotransferase (E.C. 2.4.1.19).

2. A process as set forth in claim 1, wherein said cyclodextrin glucanotransferase is produced by *Bacillus macerans, Bacillus megaterium, Bacillus circulans, Bacillus polymyxa, Bacillus stearothermophilus,* or *Klebsiella pneumoniae.*

3. A process as set forth in claims 1 or 2, wherein a mixture solution, concentration in the range of 10 to 50 w/w% and containing a liquefied starch, D.E. 3 to 40, and one or more members selected from the group consisting of fructose, sucrose, isomerized sugar and invert sugar in a ratio of donor vs. acceptor in the range of 0.2 to 5 d.s.b., is subjected to the action of said immobilized cyclodextrin glucanotransferase.

* * * * *